United States Patent [19]

Baldwin

[11] 4,411,928
[45] Oct. 25, 1983

[54] PROCESS FOR APPLYING A WATER AND ALCOHOL REPELLENT MICROBIOCIDAL FINISH TO A FABRIC AND PRODUCT SO PRODUCED

[75] Inventor: A. Frank Baldwin, Greensboro, N.C.

[73] Assignee: Burlington Industries, Inc., Greensboro, N.C.

[21] Appl. No.: 352,057

[22] Filed: Feb. 24, 1982

Related U.S. Application Data

[63] Continuation-in-part of Ser. No. 310,416, Oct. 9, 1981, and a continuation-in-part of Ser. No. 310,414, Oct. 9, 1981.

[51] Int. Cl.³ .............................................. B05D 3/02
[52] U.S. Cl. ....................................... 427/2; 427/389; 427/389.9; 427/393.1; 427/393.4
[58] Field of Search .................... 427/2, 393.1, 393.4, 427/389, 389.9

[56] References Cited

U.S. PATENT DOCUMENTS 3,991,237 11/1976 Töpfl et al. ...................... 427/389 X
4,211,815 7/1980 Deiner .......................... 427/393.4 X
4,219,625 8/1980 Mares et al. ................. 427/393.4 X

*Primary Examiner*—Michael R. Lusignan
*Assistant Examiner*—Thurman K. Page
*Attorney, Agent, or Firm*—Cushman, Darby & Cushman

[57] ABSTRACT

Non-woven fabrics are rendered repellent to water, saline, body fluids and solvents according to the disclosed process that applied bioactive finish that becomes substantive on the fabric and serves to destroy migrating and cross-contaminating bacteria, algae and fungi. The finish serves to lower the amount of microbial contamination while providing a barrier to liquid penetration. Fabrics so treated are useful as surgeon's gowns, medical drapes, isolation gowns, instrument wraps and the like.

9 Claims, No Drawings

PROCESS FOR APPLYING A WATER AND ALCOHOL REPELLENT MICROBIOCIDAL FINISH TO A FABRIC AND PRODUCT SO PRODUCED

CROSS-REFERENCE TO RELATED APPLICATIONS

This application is a continuation-in-part of my earlier applications Ser. No. 310,416 and 310,414 both filed Oct. 9, 1981.

This invention relates to a process for finishing a non-woven fabric suitable for use as a surgeon's gown, surgical drape, isolation gown, instrument wrap or the like where reduction of infection and a barrier to liquid penetration and contamination is desired. The finish of my invention becomes substantive on the fabric and serves to destroy migrating and cross-contaminating bacteria, fungi and algae. Such fabric is highly repellent to water, saline solution, body fluids and solvents, including isopropanol, is bioactive and serves to lower the amount of microbial contamination while providing a barrier to liquid contamination. One preferred use is a hospital gown of the single use or "throw away" type.

BACKGROUND OF THE INVENTION

A need exists for a hospital gown, instrument wrap or like product that is water and solvent repellent, kills bacteria but is itself non-toxic, that provides permanent antimicrobial capacity yet the antimicrobial agent itself is not extracted from the fabric in use, and that maintains its microbiocidal and repellency effectiveness over a period of time but is not inhibited by sterilization, storage or handling.

A particularly useful antimicrobial agent is DC-Q9-5700 available from Dow Corning Corporation of Midland, Michigan. The material is a silicone quaternary amine, chemically 3-(trimethoxysilyl)-propyloctadecyl dimethyl ammonium chloride, and is typically supplied in a 42% solids solution in methanol. This material has been used to protect textiles and inhibit odor-causing bacteria and fungi which contamination may result in odor problems, discoloration and deterioration of these textiles. Application of this type of silicone quaternary amine onto the surface of textiles has been found to inhibit the growth of microorganisms and to aid in the control of the above-mentioned problems. As such it is authorized by the Environmental Protection Agency of the United States Government for use on textile surfaces (EPA No. 34292-1) and it has also been accepted by the Food and Drug Administration of the U.S. Government for use in medical devices for use association with humans and animals.

Surgical drapes, hospital gowns, instrument wraps and like materials are typically made of non-woven textiles or other non-woven type materials. When such silicone quaternary amines are applied to a non-woven substrate it was found that the substrate was rendered partially hydrophobic, but not sufficient to repel body fluids, alcohol and like liquids typically present in a hospital environment.

The requirements for a successful medical fabric or substrate include the following:

1. Bioactivity—the substrate must be bioactive, that is it must achieve a 95% or better bactericidal effect within one hour. In other words, the material is bacteriocidal and not merely bacteriostatic as is the case with the treated wearing apparel discussed above.
2. Non-leachability—the bioactive/bactericidal material must remain on the substrate and not be leached from the substrate, but if leaching occurs it must be virtually undetectable, i.e. only less than 70 parts per billion (70 ppb) from a $1\frac{1}{2}$ inch $\times 1\frac{1}{2}$ inch swatch according to test procedures, described in more detail below. Non-leachability or substantial non-leachability is a factor of the fabric sample or swatch size being tested.
3. International Nonwovens and Disposables Association—The fabric must be water repellent as measured by (INDA) test IST 80.7-70 (R77), referred to herein as the mason jar test. In this test a swatch of sample fabric is placed over the mouth of a mason jar containing sufficient normal saline (0.9% NaCl) that when the jar is inverted a 4.5" head of water results. The top ring is screwed onto the jar, the jar is inverted and placed on a glass plate. The inverted jar is observed and the time is measured until the jar leaks. The minimum time for a successful sample is 30 minutes for an instrument wrap fabric, and 45 minutes for a hospital gown fabric. In any event, an average time for successful fabrics is at least one hour after which the test is stopped.
4. Spray rating, a measure of water repellency—the subject fabric should be rated to have a minimum value of 75 according to the American Association of Textile Chemists and Colorists (AATCC) spray rating test 22-1971. In this test the fabric is held tightly on a metal hoop and sprayed with 250 ml. of water. The fabric is then rated by comparison of the sprayed fabric with pictures on a standard chart.
5. Alcohol repellency—is measured in a test in the manner of INDA test IST 80.9-74 (R77) which uses ethanol wherein for my comparisons and measurements isopropanol was the alcohol that was used. In this test equal amounts of serially diluted isopropanol solutions, ranging from 60% to 100% in increments of 10 percent, are placed on a sample fabric arranged on a flat surface such as a laboratory counter top. After five minutes the surface is usually inspected and the highest concentration retained by the sample fabric is noted. The minimum value is a 70% isopropanol solution, i.e. a 70% isopropanol solution is retained by the fabric but the 80% solution penetrates through the fabric to the underlying surface. The minimum value is 70%; fabrics according to my invention typically retain 80% and 90% isopropanol solutions.
6. Static decay—this is a measure of dissipation of static electricity from the fabric and is required in surgical environments where combustible gases are present. Static decay is measured according to NFPA test 56A in which a test fabric is placed in a meter (model 406B, Electro-Tech Systems) and charged to 5,000 volts DC. The meter measures the time, in seconds, required to deplete to 10% of the original charge or 500 volts DC; minimum values for this test are about 0.5 seconds, although preferred values are less than 0.2 seconds.
7. Cytotoxicity—the leachate removed from a sample of the medical substrate must not exhibit cytotoxicity to cells. This includes not only the antimicrobial agent itself but also other finishes, colorants or the like that may also be applied to the substrate. A typical testing procedure includes adding a standardized cell culture to a leachate recovered from a predetermined sample size of the substrate being tested, incubating the culture plus leachate and observing the culture for either cell death or morphological change to the cells in the culture.

8. The medical substrate must be non-flammable in accordance with standard CS-191-53.
9. Fastness—Although not required for certain end uses, if a dye is applied it must stay on the substrate and be fixed thereto thus free from crocking and water bleeding.

DETAILED DESCRIPTION OF THE INVENTION

I have found, and hereby disclose, a process for preparing a water and alcohol repellent, bacteriostatic non-woven medical substrate in which a solution of a specific silicone quaternary amine is applied together with a water-repelling fluorocarbon and a wax/resin fluorocarbon extender, to produce the desired repellent surface. The resulting fabric also forms part of my invention.

According to the procedure of this invention a finishing bath is prepared containing the following ingredients:

| | Ingredient | Amount* |
|---|---|---|
| (1) | a $C_1$-$C_4$ alcohol, typically isopropanol or methanol, as a fugative surfactant | 0.5-0.3 |
| (2) | 3-(trimethoxysilyl)-propyloctadecyl dimethyl ammonium chloride as the microbiocide (42% solids) | 0.4-2.4 |
| (3) | a cationic wax resin as fluorocarbon extender to provide water repellency | 1.0-6.0 |
| (4) | a water repellent fluorochemical | 1.25-5.0 |
| (5) | monovalent salt, such as sodium chloride, as an antistat | 0.2-0.5 |
| (6) | water, sufficient to make | 100% |

*In percent by weight of the bath

The nature of each of these ingredients is explained below in more detail. The order of mixing these components together is also significant, that is it is generally in the order listed, and this too is explained in more detail below.

Suitable non-woven substrates are used in the process of my invention are predominantly cellulosic in nature and include paper, cotton, rayon and possibly wool, but not the substrates composed essentially entirely of an acrylic, polyester or nylon fiber. The preferred substrate is a spunlaced, non-woven material and contains about 55-75% by weight paper (cellulose) with 25-45% polyester by weight. This material is available from DuPont under the trademark SONTARA, styles 8801, 8803 and 8804.

In the procedure of my invention a non-woven substrate is directed from a supply reel through a pad bath (the content of which is explained below) and passed through a nip roll and squeezed to achieve an overall wet pickup (wpu) of between about 100 and 130% calculated on the weight of the non-woven substrate. Next the impregnated substrate is dried on the frame in a "flash" drying operation, i.e. the fabric will achieve a temperature in the range of between 325° F. and 400° F.; drying time is between 10 and 18 seconds at the temperature stated. I have found that fabric temperatures in excess of about 400° F. will greatly reduce the alcohol repellency of the fabric; on the other hand if heating is not sufficient the water repellency is lost. The skilled operator will have no difficulty in determining suitable operational parameters from the information given herein. The dried, finished product is then rolled and stored wrapped in plastic bags or the like. Other methods within the skill of the art may be used to apply the finish to the substrate.

The preferred silicone quaternary amine bioactive material is 3-(trimethoxysilyl)-propyloctadecyl-dimethyl ammonium chloride which is described in U.S. Pat. No. 3,730,701, the disclosure of which is hereby incorporated by reference. A class of suitable bioactive silyl quaternary amine compounds have the formula:

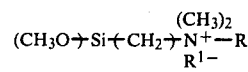

in which R is a $C_{11-22}$ alkyl group and $R^1$ is chlorine or bromine. The preferred silicone quaternary amine is 3-(trimethoxysilyl)-propyloctadecyl dimethyl ammonium chloride and is available as a 42% active solids in methanol from Dow Corning Corporation of Midland, Michigan under the designation DC-5700 (formerly Q9-5700). This material is well accepted in commerce and has been approved not only as a bacteriostatic textile treatment but also as a bactericidal component for medical device/non-drug applications.

An alcohol or mixture of alcohols is included as a fugative surfactant to lower the surface tension of the water, the major ingredient of the bath. The alcohol is evaporated off during the drying process. An alcohol or mixture of alcohols in the C-1 to C-4 carbon atom range may be used; the choice of a particular alcohol will depend upon the user. Methanol is the cheapest, however the more costly isopropanol proves to be a better surfactant.

The fluorocarbon repellent component is typically a dispersion of fluoropolymer in water. See generally Fluorine-Containing Polymers, Encyclopedia of Polymer Science & Technology, pp. 179-203, Interscience, 1967, the disclosure of which is hereby incorporated by reference. The fluoropolymer component may be selected from a host of commercially available products including DuPont's Zonyl NWG, Zonyl NWF, Zepel RS, Zepel RN and 3-M's FC-831, FC-834 and FC-461. It is the fluorocarbon component that provides alcohol repellency to the finished fabric; the requisite amount of fluorocarbon component needed to achieve the alcohol repellency desired (see test No. 5, above) is used. One will select a repellent fluorocarbon component that is compatible with the system, i.e. the other bath components and processing conditions, is economical and provides the required alcohol repellency. As the fluorocarbon component is more expensive than the wax/resin extender, described below, it is desirable to use the smallest amount of the more expensive component as possible.

The wax/resin component is well known in the art as a fluorocarbon extender. These materials are typically available in emulsions with a cationic or nonionic emulsifier. Suitable wax/resin fluorocarbon extenders commercially available include: Aerotex Repellent 96 a water dispersible wax resin containing reactive nitrogenous compounds available from American Cyanamid; Norane 193, a high molecular weight hydrophobic resin/wax complex, and Norane 88, both available from Sun Chemical Company; and Nalan W, a thermosetting resin condensate and Nalan GN, a polymer wax dispersion both available from DuPont. The wax/resin extender provides the finished fabric with the water repellency desired, serves to stabilize the silicone quaternary amine present in the bath and of course, allow for a reduction in the amount of the more expensive fluorocarbon repellent component.

A minor amount of monovalent salt, typically sodium chloride, is added to the bath in order to enhance the antistatic property of the finished fabric. Suitable salts include sodium dihydrogen phosphate and sodium chloride; divalent salts such as calcium chloride should not be used. The salt when present in the finish accepts moisture from the surrounding atmosphere and readily ionizes, thus enhancing the antistatic properties of the fabric. The required amount of salt is dissolved in water then added to the bath.

The order of addition of the various ingredients is important and is in the order 1-5 given above, except that one starts with the water component (6) into which the other ingredients are dissolved or solubilized.

During operation it is important to maintain the pad bath in the temperature range of about 50° F. to about 100° F.; lower temperatures are inefficient while higher temperatures may cause the bath to gel. The bath may be applied by pad/dip/squeeze, as illustrated above, by spraying onto the fabric, with a kiss roll or other suitable wet processing method.

The fabric produced in accordance with the present invention will demonstrate the following properties:
bioactive—95%+bactericidal in 1 hour
non-leachable—less than 70 ppb
water repellent—45 minutes minimum (mason jar)
spray rating—75 or greater
alcohol repellent—70% isopropanol or better
static decay—less than 0.5 seconds

What is claimed is:

1. A process for making a bioactive, water and alcohol repellent medical fabric comprising the steps of:
(a) applying a finishing bath composed, in percent by weight of the bath, of:

| | |
|---|---|
| a C$_1$-C$_4$ alcohol | 0.5-3.0% |
| 3-(trimethoxysilyl)- | |
| propyloctadecyl dimethyl | |
| ammonium chloride | 0.4-2.4% |
| a fluoropolymer alcohol repellent | 1.25-5.0% |
| wax/resin fluoropolymer extender | 1.0-6.0% |
| monovalent salt antistat | 0.2-0.5% |
| water | balance |

(b) drying the thus coated substrate to fix the coating to the non-woven substrate and provide a bioactive, water and alcohol repellent finished fabric.

2. The process of claim 1 wherein the finishing bath is applied in step (a) at about 100 to about 130% wet add-on before drying.

3. The process of claim 1 or 2 wherein step (b) is conducted at a temperature in the range of about 325° F. to about 400° F.

4. The process of claim 1 wherein said substrate is a spunlaced non-woven fabric containing from about 55 to 75% by weight cellulose and about 45 to about 25% polyester.

5. A process for imparting bioactive, water repellent and alcohol repellent properties to a non-woven cellulose-containing fabric comprising the steps of:
(i) applying a bioactive amount of a silyl quaternary amine compound of the formula:

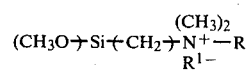

wherein R is C$_{11}$-C$_{22}$ alkyl group
and R$_1$ is bromine or chlorine; together with an alcohol and water repellent amount of a mixture of a fluoropolymer repellent composition with a resin/wax fluoropolymer extender, and
(ii) drying the thus coated fabric to produce a bioactive, water-repellent, alcohol-repellent fabric having the bioactive material attached thereto and substantially completely non-leachable therefrom.

6. The process of claim 5 wherein the silyl quaternary amine is 3-(trimethoxysilyl)-propyloctadecane or a salt thereof.

7. The process of claim 5 or 6 wherein the fabric is a spunlaced non-woven fabric containing from about 55 to 75% by weight cellulose and about 45 to 25% polyester.

8. The water and alcohol repellent bioactive fabric produced by the process of claim 1.

9. The water and alcohol repellent bioactive fabric produced by the process of claim 5.

* * * * *

UNITED STATES PATENT AND TRADEMARK OFFICE
Certificate

Patent No. 4,411,928            Patented October 25, 1983

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is A. Frank Baldwin, Greensboro, N.C.; Stuart P. Suskind, Valencia, Calif.; Donald M. Patterson, El Paso, Tex.

Signed and Sealed this nineteenth Day of August, 1986.

BRADLEY R. GARRIS,
*Office of the Deputy Assistant Commissioner for Patents.*